(12) United States Patent
Yamagata et al.

(10) Patent No.: US 9,625,452 B2
(45) Date of Patent: Apr. 18, 2017

(54) METHOD FOR ESTIMATING GFR (GLOMERULAR FILTRATION RATE) FROM MEASURED VALUE OF MEGALIN IN URINE

(71) Applicant: Denka Seiken Co., Ltd., Chuo-ku, Tokyo (JP)

(72) Inventors: Kunihiro Yamagata, Tsukuba (JP); Akira Hiwatashi, Tsukuba (JP); Masahiro Hagiwara, Tsukuba (JP); Hiroyuki Kurosawa, Gosen (JP); Yoshiaki Hirayama, Gosen (JP)

(73) Assignee: Denka Seiken Co., Ltd., Tokyo (JP)

( * ) Notice: Subject to any disclaimer, the term of this patent is extended or adjusted under 35 U.S.C. 154(b) by 0 days.

(21) Appl. No.: 14/768,527

(22) PCT Filed: Feb. 19, 2014

(86) PCT No.: PCT/JP2014/053871
§ 371 (c)(1),
(2) Date: Aug. 18, 2015

(87) PCT Pub. No.: WO2014/129490
PCT Pub. Date: Aug. 28, 2014

(65) Prior Publication Data
US 2016/0003810 A1 Jan. 7, 2016

(30) Foreign Application Priority Data
Feb. 19, 2013 (JP) ................................. 2013-030206

(51) Int. Cl.
*G01N 33/53* (2006.01)
*G01N 33/566* (2006.01)
*G01N 33/493* (2006.01)

(52) U.S. Cl.
CPC ....... *G01N 33/5308* (2013.01); *G01N 33/566* (2013.01); *G01N 33/493* (2013.01); *G01N 2333/47* (2013.01); *G01N 2800/347* (2013.01)

(58) Field of Classification Search
None
See application file for complete search history.

(56) References Cited

U.S. PATENT DOCUMENTS

| 2004/0058395 | A1 | 3/2004 | Hara |
| 2012/0040374 | A1 | 2/2012 | Saito et al. |
| 2012/0058489 | A1 | 3/2012 | Saito et al. |

FOREIGN PATENT DOCUMENTS

| EP | 2426496 A1 | 3/2012 |
| WO | WO 02/37099 A1 | 5/2002 |

(Continued)

OTHER PUBLICATIONS

Stevens et al. (Am. J. Kidney Dis. 2008 vol. 51, p. 395-406).*

(Continued)

*Primary Examiner* — Jacob Cheu
(74) *Attorney, Agent, or Firm* — Foley & Lardner LLP

(57) ABSTRACT

The object of the present invention is to provide a method for estimating the glomerular renal function in a convenient and non-invasive manner. As a result of intensive studies to achieve the above object, the present inventors found that there is a high correlation between the urinary megalin excretion rate and the estimated glomerular filtration rate (eGFR) in renal disease patients, and the glomerular filtration rate (GFR) can be estimated with high probability in a non-invasive manner by measuring the megalin level in the urine. This has led to the completion of the present invention.

5 Claims, 4 Drawing Sheets

(56) References Cited

FOREIGN PATENT DOCUMENTS

WO     WO 2010/126043 A1    11/2010
WO     WO 2010/126055 A1    11/2010

OTHER PUBLICATIONS

International Search Report dated Apr. 28, 2014, in PCT/JP2014/053871.
Christensen et al., "Essential Role of Megalin in Renal Proximal Tubule for Vitamin Homeostasis," J. Am. Soc. Nephrol., 1999, 10:2224-2236.
Jung et al., "Immortalized rat proximal tubule cells produce membrane bound and soluble megalin," Kidney International, 1998, 53:358-366.
Zheng et al., "Organ Distribution in Rats of Two Members of the Low-density Lipoprotein Receptor Gene Family, Gp330 and LRP/α2MR, and the Receptor-associated Protein (RAP)," The Journal of Histochemistry and Cytochemistry, 1994, 42(4):531-542.
Supplementary European Search Report dated Oct. 7, 2016, in EP 14753944.9.
Ogasawara et al., "Significance of Urinary Full-Length and Ectodomain Forms of Megalin in Patients with Type 2 Diabetes," Diabetes Care, May 1, 2012, 35(5):1112-1118.

\* cited by examiner

```
                           SEQUENCE LISTING

<160> NUMBER OF SEQ ID NOS: 2

<210> SEQ ID NO 1
<211> LENGTH: 13968
<212> TYPE: DNA
<213> ORGANISM: Homo sapiens

<400> SEQUENCE: 1
atggatcgcg ggccggcagc agtggcgtgc acgctgctcc tggctctcgt cgcctgccta      60
gcgccggcca gtggccaaga atgtgacagt gcgcattttc gctgtggaag tgggcattgc     120
atccctgcag actggaggtg tgatgggacc aaagactgtt cagatgacgc ggatgaaatt     180
ggctgcgctg ttgtgacctg ccagcagggc tatttcaagt gccagagtga gggacaatgc     240
atccccagct cctgggtgtg tgaccaagat caagactgtg atgatggctc agatgaacgt     300
caagattgct cacaaagtac atgctcaagt catcagataa catgctccaa tggtcagtgt     360
atcccaagtg aataccaggtg cgaccacgtc agagactgcc ccgatggagc tgatgagaat     420
gactgccagt acccaacatg tgagcagctt acttgtgaca atggggcctg ctataacacc     480
agtcagaagt gtgattggaa agttgattgc agggactcct cagatgaaat caactgcact     540
gagatatgct tgcacaatga gttttcatgt ggcaatggag agtgtatccc tcgtgcttat     600
gtctgtgacc atgacaatga ttgccaagac ggcagtgatg aacatgcttg caactatccg     660
acctgcggtg gttaccagtt cacttgcccc agtggccgat gcatttatca aaactgggtt     720
tgtgatggag aagatgactg taaagataat ggagatgaag atggatgtga agcggtcct      780 catgatgttc ataaatgttc cccaagagaa tggtcttgcc cagagtcggg acgatgcatc     840
tccatttata agtttgtgta tgggatttta gattgcccag gaagagaaga tgaaaacaac     900
actagtaccg gaaaatactg tagtatgact ctgtgctctg ccttgaactg ccagtaccag     960
tgccatgaga cgccgtatgg aggagcgtgt tttgtcccc caggttatat catcaaccac    1020
aatgacagcc gtacctgtgt tgagtttgat gattgccaga tatggggaat ttgtgaccag    1080
aagtgtgaaa gccgacctgg ccgtcacctg tgccactgtg aagaagggta tatcttggag    1140
cgtggacagt attgcaaagc taatgattcc tttggcgagg cctccattat cttctccaat    1200
ggtcgggatt tgttaattgg tgatattcat ggaaggagct tccggatcct agtggagtct    1260
cagaatcgtg gagtggccgt gggtgtggct ttccactatc acctgcaaag agttttttgg    1320
acagacaccg tgcaaaataa ggtttttttca gttgacatta atggtttaaa tatccaagag    1380
gttctcaatg tttctgttga accccagag aacctggctg tggactgggt taataataaa    1440
atctatctag tggaaccaa ggtcaaccgc atagatatgg taaatttgga tggaagctat    1500
cgggttaccc ttataactga aaactgggg catcctagag aattgccgt ggaccaact      1560 gttggttatt tattttctc agattgggag agccttctg gggaacctaa gctggaaagg    1620
gcattcatgg atggcagcaa ccgtaaagac ttggtgaaaa caaagctggg atggcctgct    1680 gggggtaactc tggatatgat atcgaagcgt gtttactggg ttgactctcg gtttgattac    1740
attgaaactg taacttatga tggaattcaa aggaagactg tagttcatgg aggctcctc     1800 attcctcatc ccttggagt aagcttattt gaaggtcagg tgttctttac agattggaca    1860
```

```
aagatggccg tgctgaaggc aaacaagttc acagagacca acccacaagt gtactaccag   1920
gcttccctga ggccctatgg agtgactgtt taccattccc tcagacagcc ctatgctacc   1980
aatccgtgta aagataacaa tggggctgt  gagcaggtct gtgttctcag ccacagaaca   2040
gataatgatg gtttgggttt ccgttgcaag tgcacattcg gcttccaact ggatacagat   2100
gagcgccact gcattgctgt tcagaatttc ctcatttttt catcccaagt tgctattcgt   2160
gggatcccgt tcaccttgtc tacccaggaa gatgtcatgg ttccagtttc ggggaatcct   2220
tctttctttg tcgggattga ttttgacgcc caggacagca ctatctttt  ttcagatatg   2280 tcaaaacaca tgattttaa  gcaaaagatt gatggcacag gaagagaaat tctcgcagct   2340
aacagggtgg aaaatgttga agtttggct  tttgattgga tttcaaagaa tctctattgg   2400
acagactctc attacaagag tatcagtgtc atgaggctag ctgataaaac gagacgcaca   2460
gtagttcagt atttaaataa cccacggtcg gtggtagttc atcctttgc  cgggtatcta   2520 ttcttcactg attggttccg tcctgctaaa attatgagag catggagtga cggatctcac   2580
ctcttgcctg taataaacac tactcttgga tgcccaatg  gcttggccat cgattgggct   2640
gcttcacgat tgtactgggt agatgcctat tttgataaaa ttgagcacag cacctttgat   2700
ggtttagaca gaagaagact gggccatata gagcagatga cacatccgtt tggacttgcc   2760
atctttggag agcatttatt ttttactgac tggagactgg gtgccattat tcgagtcagg   2820
aaagcagatg gtggagaaat gacagttatc cgaagtggca ttgcttacat actgcatttg   2880
aaatcgtatg atgtcaacat ccagactggt tctaacgcct gtaatcaacc cacgcatcct   2940
aacggtgact gcagccactt ctgcttcccg gtgccaaatt tccagcgagt gtgtgggtgc   3000
ccttatggaa tgaggctggc ttccaatcac ttgacatgcg aggggaccc  aaccaatgaa   3060 ccacccacgg agcagtgtgg cttatttccc ttcccctgta aaaatggcag atgtgtgccc   3120
aattactatc tctgtgatgg agtcgatgat tgtcatgata acagtgatga gcaactatgt   3180
ggcacactta ataatacctg ttcatcttcg gcgttcacct gtggccatgg ggagtgcatt   3240
cctgcacact ggcgctgtga caaacgcaac gactgtgtgg atggcagtga tgagcacaac   3300
tgccccaccc acgcacctgc ttcctgcctt gacacccaat acacctgtga taatcaccag   3360
tgtatctcaa agaactgggt ctgtgacaca gacaatgatt gtggggatgg atctgatgaa   3420
aagaactgca attcgacaga gacatgccaa cctagtcagt ttaattgccc caatcatcga   3480
tgtattgacc tatcgtttgt ctgtgatggt gacaaggatt tgttgatgg  atctgatgag   3540 gttggttgtg tattaaactg tactgcttct caattcaagt gtgccagtgg ggataaatgt   3600
attggcgtca caaatcgttg tgatggtgtt tttgattgca gtgacaactc ggatgaagcg   3660
ggctgtccaa ccaggcctcc tggtatgtgc cactcagatg aatttcagtg ccaagaagat   3720
ggtatctgca tcccgaactt ctgggaatgt gatgggcatc cagactgcct ctatggatct   3780
gatgagcaca atgcctgtgt ccccaagact tgcccttcat catatttcca ctgtgacaac   3840
ggaaactgca tccacagggc atggctctgt gatcgggaca atgactgcgg ggatatgagt   3900
gatgagaagg actgccctac tcagcccttt cgctgtccta gttggcaatg gcagtgtctt   3960
ggccataaca tctgtgtgaa tctgagtgta gtgtgtgatg gcatctttga ctgccccaat   4020
gggacagatg agtccccact ttgcaatggg aacagctgct cagatttcaa tggtggttgt   4080
actcacgagt gtgttcaaga gccctttggg gctaaatgcc tatgtccatt gggattctta   4140
cttgccaatg attctaagac ctgtgaagac atagatgaat gtgatattct aggctcttgt   4200
```

```
agccagcact gttacaatat gagaggttct ttccggtgct cgtgtgatac aggctacatg    4260
ttagaaagtg atgggaggac ttgcaaagtt acagcatctg agagtctgct gttacttgtg    4320
gcaagtcaga acaaaattat tgccgacagt gtcacctccc aggtccacaa tatctattca    4380
ttggtcgaga atggttctta cattgtagct gttgattttg attcaattag tggtcgtatc    4440
ttttggtctg atgcaactca gggtaaaacc tggagtgcgt ttcaaaatgg aacggacaga    4500
agagtggtat ttgacagtag catcatcttg actgaaacta ttgcaataga ttgggtaggt    4560
cgtaatcttt actggacaga ctatgctctg gaaacaattg aagtctccaa aattgatggg    4620
agccacagga ctgtgctgat tagtaaaaac ctaacaaatc caagaggact agcattagat    4680
cccagaatga atgagcatct actgttctgg tctgactggg gccaccaccc tcgcatcgag    4740
cgagccagca tggacggcag catgcgcact gtcattgtcc aggacaagat cttctggccc    4800
tgcggcttaa ctattgacta ccccaacaga ctgctctact tcatggactc ctatcttgat    4860
tacatggact tttgcgatta taatggacac catcggagac aggtgatagc cagtgatttg    4920
attatacggc accctatgc cctaactctc tttgaagact ctgtgtactg gactgaccgt    4980
gctactcgtc gggttatgcg agccaacaag tggcatggag ggaaccagtc agttgtaatg    5040
tataatattc aatggcccct tgggattgtt gcggttcatc cttcgaaaca accaaattcc    5100
gtgaatccat gtgccttttc ccgctgcagc catctctgcc tgctttcctc acaggggcct    5160 cattttact cctgtgtttg tccttcagga tggagtctgt ctcctgatct cctgaattgc    5220
ttgagagatg atcaaccttt cttaataact gtaaggcaac atataatttt tggaatctcc    5280
cttaatcctg aggtgaagag caatgatgct atggtcccca tagcagggat acagaatggt    5340
ttagatgttg aatttgatga tgctgagcaa tacatctatt gggttgaaaa tccaggtgaa    5400
attcacagag tgaagacaga tggcaccaac aggacagtat ttgcttctat atctatggtg    5460
gggccttcta tgaacctggc cttagattgg atttcaagaa acctttattc taccaatcct    5520
agaactcagt caatcgaggt tttgacactc acggagata tcagatacag aaaaacattg    5580
attgccaatg atgggacagc tcttggagtt ggcttttcaa ttggcataac tgttgatcct    5640
gctcgtggga agctgtactg gtcagaccaa ggaactgaca gtggggttcc tgccaagatc    5700
gccagtgcta acatggatgg cacatctgtg aaaactctct ttactgggaa cctcgaacac    5760
ctggagtgtg tcactcttga catcgaagag cagaaactct actgggcagt cactggaaga    5820
ggagtgattg aaagaggaaa cgtggatgga acagatcgga tgatcctggt acaccagctt    5880
tcccacccct ggggaattgc agtccatgat tcttcctttt attatactga tgaacagtat    5940
gaggtcattg aaagagttga taaggccact ggggccaaca aaatagtctt gagagataat    6000
gttccaaatc tgagggtct tcaagtttat cacagacgca atgccgccga atcctcaaat    6060
ggctgtagca acaacatgaa tgcctgtcag cagatttgcc tgcctgtacc aggaggattg    6120
ttttcctgcg cctgtgccac tggatttaaa ctcaatcctg ataatcggtc ctgctctcca    6180
tataactctt tcattgttgt ttcaatgctg tctgcaatca gaggctttag cttgaaattg    6240
tcagatcatt cagaaaccat ggtgccggtg gcaggccaag gacgaaacgc actgcatgtg    6300
gatgtggatg tgtcctctgg ctttatttat tggtgtgatt ttagcagctc agtggcatct    6360
gataatgcga tccgtagaat taaaccagat ggatcttctc tgatgaacat tgtgacacat    6420
ggaataggag aaaatggagt ccggggtatt gcagtggatt gggtagcagg aaatctttat    6480
ttcaccaatg cctttgtttc tgaaacactg atagaagttc tgcggatcaa tactacttac    6540
cgccgtgttc ttcttaaagt cacagtggac atgcctaggc atattgttgt agatcccaag    6600
```

```
aacagatacc tcttctgggc tgactatggg cagagaccaa agattgagcg ttctttcctt   6660
gactgtacca atcgaacagt gcttgtgtca gagggcattg tcacaccacg ggcttggca    6720
gtggaccgaa gtgatggcta cgtttattgg gttgatgatt ctttagatat aattgcaagg   6780
attcgtatca atggagagaa ctctgaagtg attcgttatg gcagtcgtta cccaactcct   6840
tatggcatca ctgtttttga aaattctatc atatgggtag ataggaattt gaaaaagatc   6900
ttccaagcca gcaaggaacc agagaacaca gagccaccca cagtgataag agacaatatc   6960
aactggctaa gagatgtgac catctttgac aagcaagtcc agccccggtc accagcagag   7020
gtcaacaaca acccttgctt ggaaaacaat ggtgggtgct ctcatctctg ctttgctctg   7080
cctggattgc acaccccaaa atgtgactgt gcctttggga ccctgcaaag tgatggcaag   7140
aattgtgcca tttcaacaga aaatttcctc atctttgcct tgtctaattc cttgagaagc   7200
ttacacttgg accctgaaaa ccatagccca cctttccaaa caataaatgt ggaaagaact   7260
gtcatgtctc tagactatga cagtgtaagt gatagaatct acttcacaca aaatttagcc   7320
tctggagttg acagatttc ctatgccacc ctgtcttcag ggatccatac tccaactgtc    7380
attgcttcag gtatagggac tgctgatggc attgcctttg actggattac tagaagaatt   7440
tattacagtg actacctcaa ccagatgatt aattccatgg ctgaagatgg gtctaaccgc   7500
actgtgatag cccgcgttcc aaaaccaaga gcaattgtgt tagatccctg ccaagggtac   7560
ctgtactggg ctgactggga tacacatgcc aaaatcgaga gagccacatt gggaggaaac   7620
ttccgggtac ccattgtgaa cagcagtctg gtcatgccca gtgggctgac tctggactat   7680
gaagaggacc ttctctactg ggtggatgct agtctgcaga ggattgaacg cagcactctg   7740
acgggcgtgg atcgtgaagt cattgtcaat gcagccgttc atgcttttgg cttgactctc   7800
tatgccagt atatttactg gactgacttg tacacacaaa gaatttaccg agctaacaaa    7860
tatgacgggt caggtcagat tgcaatgacc acaaatttgc tctcccagcc cagggaatc    7920
aacactgttg tgaagaacca gaaacaacag tgtaacaatc cttgtgaaca gtttaatggg   7980
ggctgcagcc atatctgtgc accaggtcca aatggtgccg agtgccagtg tccacatgag   8040
ggcaactggt atttggccaa caacaggaag cactgcattg tggacaatgg tgaacgatgt   8100
ggtgcatctt ccttcacctg ctccaatggg cgctgcatct cggaagagtg gaagtgtgat   8160
aatgacaacg actgtgggga tggcagtgat gagatgaaa gtgtctgtgc acttcacacc    8220
tgctcaccga cagccttcac ctgtgccaat gggcgatgtg tccaatactc ttaccgctgt   8280
gattactaca atgactgtgg tgatggcagt gatgaggcag ggtgcctgtt cagggactgc   8340
aatgccacca cggagtttat gtgcaataac agaaggtgca tacctcgtga gtttatctgc   8400
aatggtgtag acaactgcca tgataataac acttcagatg agaaaaattg ccctgatcgc   8460
acttgccagt ctggatacac aaaatgtcat aattcaaata tttgtattcc tcgcgtttat   8520
ttgtgtgacg gagacaatga ctgtggagat aacagtgatg aaaaccctac ttattgcacc   8580
actcacacat gcagcagcag tgagttccaa tgcgcatctg ggcgctgtat tcctcaacat   8640
tggtattgtg atcaagaaac agattgtttt gatgcctctg atgaacctgc tcttgtggt    8700
cactctgagc gaacatgcct agctgatgag ttcaagtgta tggtgggag gtgcatccca    8760
agcgaatgga tctgtgacgg tgataatgac tgtggggata tgagtgacga ggataaaagg   8820
caccagtgtc agaatcaaaa ctgctcggat tccgagtttc tctgtgtaaa tgacagacct   8880
ccggacagga ggtgcattcc ccagtcttgg gtctgtgatg gcgatgtgga ttgtactgac   8940
```

```
ggctacgatg agaatcagaa ttgcaccagg agaacttgct ctgaaaatga attcacctgt   9000
ggttacggac tgtgtatccc aaagatattc aggtgtgacc ggcacaatga ctgtggtgac   9060
tatagcgacg agaggggctg cttataccag acttgccaac agaatcagtt tacctgtcag   9120
aacgggcgct gcattagtaa aaccttcgtc tgtgatgagg ataatgactg tggagacgga   9180
tctgatgagc tgatgcacct gtgccacacc ccagaaccca cgtgtccacc tcacgagttc   9240
aagtgtgaca atgggcgctg catcgagatg atgaaactct gcaaccacct agatgactgt   9300
ttggacaaca gcgatgagaa aggctgtggc attaatgaat gccatgaccc ttcaatcagt   9360
ggctgcgatc acaactgcac agacacctta accagtttct attgttcctg tcgtcctggt   9420
tacaagctca tgtctgacaa gcggacttgt gttgatattg atgaatgcac agagatgcct   9480
tttgtctgta gccagaagtg tgagaatgta ataggctcct acatctgtaa gtgtgcccca   9540
ggctacctcc gagaaccaga tggaaagacc tgccggcaaa acagtaacat cgaaccctat   9600
ctcatttta gcaaccgtta ctatttgaga aatttaacta tagatggcta tttttactcc   9660
ctcatcttgg aaggactgga caatgttgtg gcattagatt ttgaccgagt agagaagaga   9720
ttgtattgga ttgatacaca gaggcaagtc attgagagaa tgtttctgaa taagacaaac   9780
aaggagacaa tcataaacca cagactacca gctgcagaaa gtctggctgt agactgggtt   9840
tccagaaagc tctactggtt ggatgcccgc ctggatggcc tctttgtctc tgacctcaat   9900
ggtgacacc gccgcatgct ggcccagcac tgtgtggatg ccaacaacac cttctgcttt   9960
gataatccca gaggacttgc ccttcaccct caatatgggt acctctactg ggcagactgg  10020
ggtcaccgcg catacattgg gagagtaggc atggatggaa ccaacaagtc tgtgataatc  10080
tccaccaagt tagagtggcc taatggcatc accattgatt acaccaatga tctactctac  10140
tgggcagatg cccacctggg ttacatagag tactctgatt tggagggcca ccatcgcacac 10200
acggtgtatg atggggcact gcctcacccct ttcgctatta ccattttga agacactatt  10260
tattggacag attggaatac aaggacagtg gaaaagggaa acaaatatga tggatcaaat  10320
agacagacac tggtgaacac aacacacaga ccatttgaca tccatgtgta ccatccatat  10380
aggcagccca ttgtgagcaa tccctgtggt accaacaatg gtggctgttc tcatctctgc  10440
ctcatcaagc caggaggaaa agggttcact tgcgagtgtc cagatgactt ccgcaccctt  10500
caactgagtg gcagcaccta ctgcatgccc atgtgctcca gcacccagtt cctgtgcgct  10560
aacaatgaaa agtgcattcc tatctggtgg aaatgtgatg gacagaaaga ctgctcagat  10620
ggctctgatg aactggccct ttgcccgcag cgcttctgcc gactgggaca gttccagtgc  10680
agtgacggca actgcaccag cccgcagact ttatgcaatg ctcaccaaaa ttgccctgat  10740
gggtctgatg aagaccgtct tctttgtgag aatcaccact gtgactccaa tgaatggcag  10800
tgcgccaaca acgttgcat cccagaatcc tggcagtgtg acacatttaa cgactgtgag 10860
gataactcag atgaagacag ttcccactgt gccagcagga cctgccggcc gggccagttt  10920
cggtgtgcta atgccgctg catcccgcag gcctggaagt gtgatgtgga taatgattgt  10980
ggagaccact cggatgagcc cattgaagaa tgcatgagct ctgcccatct ctgtgacaac  11040
ttcacagaat tcagctgcaa aacaaattac cgctgcatcc caagtgggc cgtgtgcaat  11100
ggtgtagatg actgcaggga caacagtgat gagcaaggct gtgaggagag gacatgccat  11160
cctgtggggg atttccgctg taaaaatcac cactgcatcc ctcttcgttg gcagtgtgat  11220
gggcaaaatg actgtggaga taactcagat gaggaaaact gtgctccccg ggagtgcaca  11280
gagagcgagt ttcgatgtgt caatcagcag tgcattccct cgcgatggat ctgtgaccat  11340
```

```
tacaacgact gtggggacaa ctcagatgaa cgggactgtg agatgaggac ctgccatcct   11400
gaatattttc agtgtacaag tggacattgt gtacacagtg aactgaaatg cgatggatcc   11460
gctgactgtt tggatgcgtc tgatgaagct gattgtccca cacgctttcc tgatggtgca   11520
tactgccagg ctactatgtt cgaatgcaaa aaccatgttt gtatcccgcc atattggaaa   11580
tgtgatggcg atgatgactg tggcgatggt tcagatgaag aacttcacct gtgcttggat   11640
gttccctgta attcaccaaa ccgttttccgg tgtgacaaca atcgctgcat ttatagtcat   11700
gaggtgtgca atggtgtgga tgactgtgga gatggaactg atgagacaga ggagcactgt   11760
agaaaaccga cccctaaacc ttgtacagaa tatgaatata agtgtggcaa tgggcattgc   11820
attccacatg acaatgtgtg tgatgatgcc gatgactgtg gtgactggtc cgatgaactg   11880
ggttgcaata aaggaaaaga aagaacatgt gctgaaaata tatgcgagca aaattgtacc   11940
caattaaatg aaggaggatt tatctgctcc tgtacagctg ggttcgaaac caatgttttt   12000
gacagaacct cctgtctaga tatcaatgaa tgtgaacaat ttgggacttg tccccagcac   12060
tgcagaaata ccaaaggaag ttatgagtgt gtctgtctgg atggcttcac gtctatgagt   12120
gaccgccctg gaaaacgatg tgcagctgag ggtagctctc ctttgttgct actgcctgac   12180
aatgtccgaa ttcgaaaata taatctctca tctgagaggt tctcagagta tcttcaagat   12240
gaggaatata tccaagctgt tgattatgat tgggatccca aggacatagg cctcagtgtt   12300
gtgtattaca ctgtgcgagg ggagggctct aggtttggtg ctatcaaacg tgcctacatc   12360
cccaactttg aatccggccg caataatctt gtgcaggaag ttgacctgaa actgaaatac   12420
gtaatgcagc cagatggaat agcagtggac tgggttggaa ggcatattta ctggtcagat   12480
gtcaagaata aacgcattga ggtggctaaa cttgatggaa ggtacagaaa gtggctgatt   12540
tccactgacc tggaccaacc agctgctatt gctgtgaatc ccaaactagg gcttatgttc   12600
tggactgact ggggaaagga acctaaaatc gagtctgcct ggatgaatgg agaggaccgc   12660
aacatcctgg ttttcgagga ccttggttgg ccaactggcc tttctatcga ttatttgaac   12720
aatgaccgaa tctactggag tgacttcaag gaggacgtta ttgaaaccat aaaatatgat   12780
gggactgata ggagagtcat tgcaaaggaa gcaatgaacc cttacagcct ggacatcttt   12840
gaagaccagt tatactggat atctaaggaa aagggagaag tatggaaaca aaataaattt   12900
gggcaaggaa agaagagaa aacgctggta gtgaacccctt ggctcactca agttcgaatc   12960
tttcatcaac tcagatacaa taagtcagtg cccaaccttt gcaaacagat ctgcagccac   13020
ctctgccttc tgagacctgg aggatacagc tgtgcctgtc cccaaggctc agctttata   13080 gaggggagca ccactgagtg tgatgcagcc atcgaactgc ctatcaacct gccccccccca   13140 tgcaggtgca tgcacggagg aaattgctat tttgatgaga ctgacctccc caaatgcaag   13200
tgtcctagcg gctacaccgg aaaatattgt gaaatggcgt tttcaaaagg catctctcca   13260
ggaacaaccg cagtagctgt gctgttgaca atcctcttga tcgtcgtaat tggagctctg   13320
gcaattgcag gattcttcca ctatagaagg accggctccc ttttgcctgc tctgcccaag   13380
ctgccaagct taagcagtct cgtcaagccc tctgaaaatg ggaatggggt gaccttcaga   13440
tcaggggcag atcttaacat ggatattgga gtgtctggtt ttggacctga gactgctatt   13500
gacaggtcaa tggcaatgag tgaagacttt gtcatggaaa tggggaagca gcccataata   13560
tttgaaaacc caatgtactc agccagagac agtgctgtca aagtggttca gccaatccag   13620
gtgactgtat ctgaaaatgt ggataataag aattatggaa gtcccataaa cccttctgag   13680
```

-continued

```
atagttccag agacaaaccc aacttcacca gctgctgatg gaactcaggt gacaaaatgg    13740
aatctcttca aacgaaaatc taaacaaact accaactttg aaaatccaat ctatgcacag    13800
atggagaacg agcaaaagga aagtgttgct gcgacaccac ctccatcacc ttcgctccct    13860
gctaagccta agcctccttc gagaagagac ccaactccaa cctattctgc aacagaagac    13920
acttttaaag acaccgcaaa tcttgttaaa gaagactctg aagtatag                 13968
```

<210> SEQ ID NO 2
<211> LENGTH: 4655
<212> TYPE: PRT
<213> ORGANISM: Homo sapiens
<400> SEQUENCE: 2

```
Met Asp Arg Gly Pro Ala Ala Val Ala Cys Thr Leu Leu Ala Leu
1               5                   10                  15

Val Ala Cys Leu Ala Pro Ala Ser Gly Gln Glu Cys Asp Ser Ala His
            20                  25                  30

Phe Arg Cys Gly Ser Gly His Cys Ile Pro Ala Asp Trp Arg Cys Asp
        35                  40                  45

Gly Thr Lys Asp Cys Ser Asp Asp Ala Asp Glu Ile Gly Cys Ala Val
    50                  55                  60

Val Thr Cys Gln Gln Gly Tyr Phe Lys Cys Gln Ser Glu Gly Gln Cys
65                  70                  75                  80

Ile Pro Ser Ser Trp Val Cys Asp Gln Asp Gln Cys Asp Asp Gly
                85                  90                  95

Ser Asp Glu Arg Gln Asp Cys Ser Gln Ser Thr Cys Ser Ser His Gln
            100                 105                 110

Ile Thr Cys Ser Asn Gly Gln Cys Ile Pro Ser Glu Tyr Arg Cys Asp
        115                 120                 125

His Val Arg Asp Cys Pro Asp Gly Ala Asp Glu Asn Asp Cys Gln Tyr
    130                 135                 140

Pro Thr Cys Glu Gln Leu Thr Cys Asp Asn Gly Ala Cys Tyr Asn Thr
145                 150                 155                 160

Ser Gln Lys Cys Asp Trp Lys Val Asp Cys Arg Asp Ser Ser Asp Glu
                165                 170                 175

Ile Asn Cys Thr Glu Ile Cys Leu His Asn Glu Phe Ser Cys Gly Asn
            180                 185                 190

Gly Glu Cys Ile Pro Arg Ala Tyr Val Cys Asp His Asp Asn Asp Cys
        195                 200                 205

Gln Asp Gly Ser Asp Glu His Ala Cys Asn Tyr Pro Thr Cys Gly Gly
    210                 215                 220

Tyr Gln Phe Thr Cys Pro Ser Gly Arg Cys Ile Tyr Gln Asn Trp Val
225                 230                 235                 240

Cys Asp Gly Glu Asp Asp Cys Lys Asp Asn Gly Asp Glu Asp Gly Cys
                245                 250                 255

Glu Ser Gly Pro His Asp Val Lys Cys Ser Pro Arg Glu Trp Ser
            260                 265                 270

Cys Pro Glu Ser Gly Arg Cys Ile Ser Ile Tyr Lys Val Cys Asp Gly
        275                 280                 285

Ile Leu Asp Cys Pro Gly Arg Glu Asp Glu Asn Asn Thr Ser Thr Gly
    290                 295                 300

Lys Tyr Cys Ser Met Thr Leu Cys Ser Ala Leu Asn Cys Gln Tyr Gln
305                 310                 315                 320

Cys His Glu Thr Pro Tyr Gly Gly Ala Cys Phe Cys Pro Pro Gly Tyr
```

```
                325                 330                 335
Ile Ile Asn His Asn Asp Ser Arg Thr Cys Val Glu Phe Asp Asp Cys
            340                 345                 350

Gln Ile Trp Gly Ile Cys Asp Gln Lys Cys Glu Ser Arg Pro Gly Arg
            355                 360                 365

His Leu Cys His Cys Glu Glu Gly Tyr Ile Leu Glu Arg Gly Gln Tyr
            370                 375                 380

Cys Lys Ala Asn Asp Ser Phe Gly Glu Ala Ser Ile Ile Phe Ser Asn
385                 390                 395                 400

Gly Arg Asp Leu Leu Ile Gly Asp Ile His Gly Arg Ser Phe Arg Ile
                405                 410                 415

Leu Val Glu Ser Gln Asn Arg Gly Val Ala Val Gly Val Ala Phe His
            420                 425                 430

Tyr His Leu Gln Arg Val Phe Trp Thr Asp Thr Val Gln Asn Lys Val
            435                 440                 445

Phe Ser Val Asp Ile Asn Gly Leu Asn Ile Gln Glu Val Leu Asn Val
            450                 455                 460

Ser Val Glu Thr Pro Glu Asn Leu Ala Val Asp Trp Val Asn Asn Lys
465                 470                 475                 480

Ile Tyr Leu Val Glu Thr Lys Val Asn Arg Ile Asp Met Val Asn Leu
                485                 490                 495

Asp Gly Ser Tyr Arg Val Thr Leu Ile Thr Glu Asn Leu Gly His Pro
            500                 505                 510

Arg Gly Ile Ala Val Asp Pro Thr Val Gly Tyr Leu Phe Phe Ser Asp
            515                 520                 525

Trp Glu Ser Leu Ser Gly Glu Pro Lys Leu Glu Arg Ala Phe Met Asp
            530                 535                 540

Gly Ser Asn Arg Lys Asp Leu Val Lys Thr Lys Leu Gly Trp Pro Ala
545                 550                 555                 560

Gly Val Thr Leu Asp Met Ile Ser Lys Arg Val Tyr Trp Val Asp Ser
                565                 570                 575

Arg Phe Asp Tyr Ile Glu Thr Val Thr Tyr Asp Gly Ile Gln Arg Lys
            580                 585                 590

Thr Val Val His Gly Gly Ser Leu Ile Pro His Pro Phe Gly Val Ser
            595                 600                 605

Leu Phe Glu Gly Gln Val Phe Phe Thr Asp Trp Thr Lys Met Ala Val
            610                 615                 620

Leu Lys Ala Asn Lys Phe Thr Glu Thr Asn Pro Gln Val Tyr Tyr Gln
625                 630                 635                 640

Ala Ser Leu Arg Pro Tyr Gly Val Thr Val Tyr His Ser Leu Arg Gln
                645                 650                 655

Pro Tyr Ala Thr Asn Pro Cys Lys Asp Asn Asn Gly Gly Cys Glu Gln
            660                 665                 670

Val Cys Val Leu Ser His Arg Thr Asp Asn Asp Gly Leu Gly Phe Arg
            675                 680                 685

Cys Lys Cys Thr Phe Gly Phe Gln Leu Asp Thr Asp Glu Arg His Cys
            690                 695                 700

Ile Ala Val Gln Asn Phe Leu Ile Phe Ser Ser Gln Val Ala Ile Arg
705                 710                 715                 720

Gly Ile Pro Phe Thr Leu Ser Thr Gln Glu Asp Val Met Val Pro Val
                725                 730                 735

Ser Gly Asn Pro Ser Phe Phe Val Gly Ile Asp Phe Asp Ala Gln Asp
            740                 745                 750
```

-continued

```
Ser Thr Ile Phe Phe Ser Asp Met Ser Lys His Met Ile Phe Lys Gln
        755                 760                 765

Lys Ile Asp Gly Thr Gly Arg Glu Ile Leu Ala Ala Asn Arg Val Glu
    770                 775                 780

Asn Val Glu Ser Leu Ala Phe Asp Trp Ile Ser Lys Asn Leu Tyr Trp
785                 790                 795                 800

Thr Asp Ser His Tyr Lys Ser Ile Ser Val Met Arg Leu Ala Asp Lys
                805                 810                 815

Thr Arg Arg Thr Val Val Gln Tyr Leu Asn Asn Pro Arg Ser Val Val
            820                 825                 830

Val His Pro Phe Ala Gly Tyr Leu Phe Phe Thr Asp Trp Phe Arg Pro
        835                 840                 845

Ala Lys Ile Met Arg Ala Trp Ser Asp Gly Ser His Leu Leu Pro Val
    850                 855                 860

Ile Asn Thr Thr Leu Gly Trp Pro Asn Gly Leu Ala Ile Asp Trp Ala
865                 870                 875                 880

Ala Ser Arg Leu Tyr Trp Val Asp Ala Tyr Phe Asp Lys Ile Glu His
                885                 890                 895

Ser Thr Phe Asp Gly Leu Asp Arg Arg Arg Leu Gly Ile Glu Gln
            900                 905                 910

Met Thr His Pro Phe Gly Leu Ala Ile Phe Gly Glu His Leu Phe Phe
        915                 920                 925

Thr Asp Trp Arg Leu Gly Ala Ile Ile Arg Val Arg Lys Ala Asp Gly
    930                 935                 940

Gly Glu Met Thr Val Ile Arg Ser Gly Ile Ala Tyr Ile Leu His Leu
945                 950                 955                 960

Lys Ser Tyr Asp Val Asn Ile Gln Thr Gly Ser Asn Ala Cys Asn Gln
                965                 970                 975

Pro Thr His Pro Asn Gly Asp Cys Ser His Phe Cys Phe Pro Val Pro
            980                 985                 990

Asn Phe Gln Arg Val Cys Gly Cys Pro Tyr Gly Met Arg Leu Ala Ser
        995                 1000                1005

Asn His Leu Thr Cys Glu Gly Asp Pro Thr Asn Glu Pro Pro Thr Glu
    1010                1015                1020

Gln Cys Gly Leu Phe Ser Phe Pro Cys Lys Asn Gly Arg Cys Val Pro
1025                1030                1035                1040

Asn Tyr Tyr Leu Cys Asp Gly Val Asp Asp Cys His Asp Asn Ser Asp
                1045                1050                1055

Glu Gln Leu Cys Gly Thr Leu Asn Asn Thr Cys Ser Ser Ala Phe
            1060                1065                1070

Thr Cys Gly His Gly Glu Cys Ile Pro Ala His Trp Arg Cys Asp Lys
        1075                1080                1085

Arg Asn Asp Cys Val Asp Gly Ser Asp Glu His Asn Cys Pro Thr His
    1090                1095                1100

Ala Pro Ala Ser Cys Leu Asp Thr Gln Tyr Thr Cys Asp Asn His Gln
1105                1110                1115                1120

Cys Ile Ser Lys Asn Trp Val Cys Asp Thr Asp Asn Asp Cys Gly Asp
                1125                1130                1135

Gly Ser Asp Glu Lys Asn Cys Asn Ser Thr Glu Thr Cys Gln Pro Ser
            1140                1145                1150

Gln Phe Asn Cys Pro Asn His Arg Cys Ile Asp Leu Ser Phe Val Cys
        1155                1160                1165
```

```
Asp Gly Asp Lys Asp Cys Val Asp Gly Ser Asp Glu Val Gly Cys Val
    1170            1175                1180

Leu Asn Cys Thr Ala Ser Gln Phe Lys Cys Ala Ser Gly Asp Lys Cys
1185                1190                1195                1200

Ile Gly Val Thr Asn Arg Cys Asp Gly Val Phe Asp Cys Ser Asp Asn
        1205                1210                1215

Ser Asp Glu Ala Gly Cys Pro Thr Arg Pro Gly Met Cys His Ser
        1220                1225                1230

Asp Glu Phe Gln Cys Gln Asp Gly Ile Cys Ile Pro Asn Phe Trp
        1235                1240                1245

Glu Cys Asp Gly His Pro Asp Cys Leu Tyr Gly Ser Asp Glu His Asn
        1250                1255                1260

Ala Cys Val Pro Lys Thr Cys Pro Ser Ser Tyr Phe His Cys Asp Asn
1265                1270                1275                1280

Gly Asn Cys Ile His Arg Ala Trp Leu Cys Asp Arg Asp Asn Asp Cys
            1285                1290                1295

Gly Asp Met Ser Asp Glu Lys Asp Cys Pro Thr Gln Pro Phe Arg Cys
        1300                1305                1310

Pro Ser Trp Gln Trp Gln Cys Leu Gly His Asn Ile Cys Val Asn Leu
        1315                1320                1325

Ser Val Val Cys Asp Gly Ile Phe Asp Cys Pro Asn Gly Thr Asp Glu
        1330                1335                1340

Ser Pro Leu Cys Asn Gly Asn Ser Cys Ser Asp Phe Asn Gly Gly Cys
1345                1350                1355                1360

Thr His Glu Cys Val Gln Glu Pro Phe Gly Ala Lys Cys Leu Cys Pro
            1365                1370                1375

Leu Gly Phe Leu Leu Ala Asn Asp Ser Lys Thr Cys Glu Asp Ile Asp
        1380                1385                1390

Glu Cys Asp Ile Leu Gly Ser Cys Ser Gln His Cys Tyr Asn Met Arg
        1395                1400                1405

Gly Ser Phe Arg Cys Ser Cys Asp Thr Gly Tyr Met Leu Glu Ser Asp
        1410                1415                1420

Gly Arg Thr Cys Lys Val Thr Ala Ser Glu Ser Leu Leu Leu Val
1425                1430                1435                1440

Ala Ser Gln Asn Lys Ile Ile Ala Asp Ser Val Thr Ser Gln Val His
            1445                1450                1455

Asn Ile Tyr Ser Leu Val Glu Asn Gly Ser Tyr Ile Val Ala Val Asp
        1460                1465                1470

Phe Asp Ser Ile Ser Gly Arg Ile Phe Trp Ser Asp Ala Thr Gln Gly
        1475                1480                1485

Lys Thr Trp Ser Ala Phe Gln Asn Gly Thr Asp Arg Arg Val Val Phe
        1490                1495                1500

Asp Ser Ser Ile Ile Leu Thr Glu Thr Ile Ala Ile Asp Trp Val Gly
1505                1510                1515                1520

Arg Asn Leu Tyr Trp Thr Asp Tyr Ala Leu Glu Thr Ile Glu Val Ser
            1525                1530                1535

Lys Ile Asp Gly Ser His Arg Thr Val Leu Ile Ser Lys Asn Leu Thr
        1540                1545                1550

Asn Pro Arg Gly Leu Ala Leu Asp Pro Arg Met Asn Glu His Leu Leu
        1555                1560                1565

Phe Trp Ser Asp Trp Gly His His Pro Arg Ile Glu Arg Ala Ser Met
        1570                1575                1580

Asp Gly Ser Met Arg Thr Val Ile Val Gln Asp Lys Ile Phe Trp Pro
```

-continued

```
            1585                1590                1595                1600

Cys Gly Leu Thr Ile Asp Tyr Pro Asn Arg Leu Leu Tyr Phe Met Asp
            1605                1610                1615

Ser Tyr Leu Asp Tyr Met Asp Phe Cys Asp Tyr Asn Gly His His Arg
            1620                1625                1630

Arg Gln Val Ile Ala Ser Asp Leu Ile Ile Arg His Pro Tyr Ala Leu
            1635                1640                1645

Thr Leu Phe Glu Asp Ser Val Tyr Trp Thr Arg Ala Thr Arg Arg
    1650                1655                1660

Val Met Arg Ala Asn Lys Trp His Gly Gly Asn Gln Ser Val Val Met
1665                1670                1675                1680

Tyr Asn Ile Gln Trp Pro Leu Gly Ile Val Ala Val His Pro Ser Lys
            1685                1690                1695

Gln Pro Asn Ser Val Asn Pro Cys Ala Phe Ser Arg Cys Ser His Leu
            1700                1705                1710

Cys Leu Leu Ser Ser Gln Gly Pro His Phe Tyr Ser Cys Val Cys Pro
            1715                1720                1725

Ser Gly Trp Ser Leu Ser Pro Asp Leu Leu Asn Cys Leu Arg Asp Asp
            1730                1735                1740

Gln Pro Phe Leu Ile Thr Val Arg Gln His Ile Ile Phe Gly Ile Ser
1745                1750                1755                1760

Leu Asn Pro Glu Val Lys Ser Asn Asp Ala Met Val Pro Ile Ala Gly
            1765                1770                1775

Ile Gln Asn Gly Leu Asp Val Glu Phe Asp Asp Ala Glu Gln Tyr Ile
            1780                1785                1790

Tyr Trp Val Glu Asn Pro Gly Glu Ile His Arg Val Lys Thr Asp Gly
            1795                1800                1805

Thr Asn Arg Thr Val Phe Ala Ser Ile Ser Met Val Gly Pro Ser Met
            1810                1815                1820

Asn Leu Ala Leu Asp Trp Ile Ser Arg Asn Leu Tyr Ser Thr Asn Pro
1825                1830                1835                1840

Arg Thr Gln Ser Ile Glu Val Leu Thr Leu His Gly Asp Ile Arg Tyr
            1845                1850                1855

Arg Lys Thr Leu Ile Ala Asn Asp Gly Thr Ala Leu Gly Val Gly Phe
            1860                1865                1870

Pro Ile Gly Ile Thr Val Asp Pro Ala Arg Gly Lys Leu Tyr Trp Ser
            1875                1880                1885

Asp Gln Gly Thr Asp Ser Gly Val Pro Ala Lys Ile Ala Ser Ala Asn
            1890                1895                1900

Met Asp Gly Thr Ser Val Lys Thr Leu Phe Thr Gly Asn Leu Glu His
1905                1910                1915                1920

Leu Glu Cys Val Thr Leu Asp Ile Glu Glu Gln Lys Leu Tyr Trp Ala
            1925                1930                1935

Val Thr Gly Arg Gly Val Ile Glu Arg Gly Asn Val Asp Gly Thr Asp
            1940                1945                1950

Arg Met Ile Leu Val His Gln Leu Ser His Pro Trp Gly Ile Ala Val
            1955                1960                1965

His Asp Ser Phe Leu Tyr Tyr Thr Asp Glu Gln Tyr Glu Val Ile Glu
            1970                1975                1980

Arg Val Asp Lys Ala Thr Gly Ala Asn Lys Ile Val Leu Arg Asp Asn
1985                1990                1995                2000

Val Pro Asn Leu Arg Gly Leu Gln Val Tyr His Arg Arg Asn Ala Ala
            2005                2010                2015
```

```
Glu Ser Ser Asn Gly Cys Ser Asn Asn Met Asn Ala Cys Gln Gln Ile
                2020                2025                2030

Cys Leu Pro Val Pro Gly Gly Leu Phe Ser Cys Ala Cys Ala Thr Gly
                2035                2040                2045

Phe Lys Leu Asn Pro Asp Asn Arg Ser Cys Ser Pro Tyr Asn Ser Phe
                2050                2055                2060

Ile Val Val Ser Met Leu Ser Ala Ile Arg Gly Phe Ser Leu Glu Leu
2065                2070                2075                2080

Ser Asp His Ser Glu Thr Met Val Pro Val Ala Gly Gln Gly Arg Asn
                2085                2090                2095

Ala Leu His Val Asp Val Asp Val Ser Ser Gly Phe Ile Tyr Trp Cys
                2100                2105                2110

Asp Phe Ser Ser Val Ala Ser Asp Asn Ala Ile Arg Arg Ile Lys
                2115                2120                2125

Pro Asp Gly Ser Ser Leu Met Asn Ile Val Thr His Gly Ile Gly Glu
                2130                2135                2140

Asn Gly Val Arg Gly Ile Ala Val Asp Trp Val Ala Gly Asn Leu Tyr
2145                2150                2155                2160

Phe Thr Asn Ala Phe Val Ser Glu Thr Leu Ile Glu Val Leu Arg Ile
                2165                2170                2175

Asn Thr Thr Tyr Arg Arg Val Leu Leu Lys Val Thr Val Asp Met Pro
                2180                2185                2190

Arg His Ile Val Val Asp Pro Lys Asn Arg Tyr Leu Phe Trp Ala Asp
                2195                2200                2205

Tyr Gly Gln Arg Pro Lys Ile Glu Arg Ser Phe Leu Asp Cys Thr Asn
                2210                2215                2220

Arg Thr Val Leu Val Ser Glu Gly Ile Val Thr Pro Arg Gly Leu Ala
2225                2230                2235                2240

Val Asp Arg Ser Asp Gly Tyr Val Tyr Trp Val Asp Asp Ser Leu Asp
                2245                2250                2255

Ile Ile Ala Arg Ile Arg Ile Asn Gly Glu Asn Ser Glu Val Ile Arg
                2260                2265                2270

Tyr Gly Ser Arg Tyr Pro Thr Pro Tyr Gly Ile Thr Val Phe Glu Asn
                2275                2280                2285

Ser Ile Ile Trp Val Asp Arg Asn Leu Lys Lys Ile Phe Gln Ala Ser
                2290                2295                2300

Lys Glu Pro Glu Asn Thr Glu Pro Pro Thr Val Ile Arg Asp Asn Ile
2305                2310                2315                2320

Asn Trp Leu Arg Asp Val Thr Ile Phe Asp Lys Gln Val Gln Pro Arg
                2325                2330                2335

Ser Pro Ala Glu Val Asn Asn Pro Cys Leu Glu Asn Asn Gly Gly
                2340                2345                2350

Cys Ser His Leu Cys Phe Ala Leu Pro Gly Leu His Thr Pro Lys Cys
                2355                2360                2365

Asp Cys Ala Phe Gly Thr Leu Gln Ser Asp Gly Lys Asn Cys Ala Ile
                2370                2375                2380

Ser Thr Glu Asn Phe Leu Ile Phe Ala Leu Ser Asn Ser Leu Arg Ser
2385                2390                2395                2400

Leu His Leu Asp Pro Glu Asn His Ser Pro Pro Phe Gln Thr Ile Asn
                2405                2410                2415

Val Glu Arg Thr Val Met Ser Leu Asp Tyr Asp Ser Val Ser Asp Arg
                2420                2425                2430
```

```
Ile Tyr Phe Thr Gln Asn Leu Ala Ser Gly Val Gln Ile Ser Tyr
            2435                2440                2445

Ala Thr Leu Ser Ser Gly Ile His Thr Pro Thr Val Ile Ala Ser Gly
            2450                2455                2460

Ile Gly Thr Ala Asp Gly Ile Ala Phe Asp Trp Ile Thr Arg Arg Ile
2465                2470                2475                2480

Tyr Tyr Ser Asp Tyr Leu Asn Gln Met Ile Asn Ser Met Ala Glu Asp
            2485                2490                2495

Gly Ser Asn Arg Thr Val Ile Ala Arg Val Pro Lys Pro Arg Ala Ile
            2500                2505                2510

Val Leu Asp Pro Cys Gln Gly Tyr Leu Tyr Trp Ala Asp Trp Asp Thr
            2515                2520                2525

His Ala Lys Ile Glu Arg Ala Thr Leu Gly Gly Asn Phe Arg Val Pro
            2530                2535                2540

Ile Val Asn Ser Ser Leu Val Met Pro Ser Gly Leu Thr Leu Asp Tyr
2545                2550                2555                2560

Glu Glu Asp Leu Leu Tyr Trp Val Asp Ala Ser Leu Gln Arg Ile Glu
            2565                2570                2575

Arg Ser Thr Leu Thr Gly Val Asp Arg Glu Val Ile Val Asn Ala Ala
            2580                2585                2590

Val His Ala Phe Gly Leu Thr Leu Tyr Gly Gln Tyr Ile Tyr Trp Thr
            2595                2600                2605

Asp Leu Tyr Thr Gln Arg Ile Tyr Arg Ala Asn Lys Tyr Asp Gly Ser
            2610                2615                2620

Gly Gln Ile Ala Met Thr Thr Asn Leu Leu Ser Gln Pro Arg Gly Ile
2625                2630                2635                2640

Asn Thr Val Val Lys Asn Gln Lys Gln Gln Cys Asn Asn Pro Cys Glu
            2645                2650                2655

Gln Phe Asn Gly Gly Cys Ser His Ile Cys Ala Pro Gly Pro Asn Gly
            2660                2665                2670

Ala Glu Cys Gln Cys Pro His Glu Gly Asn Trp Tyr Leu Ala Asn Asn
            2675                2680                2685

Arg Lys His Cys Ile Val Asp Asn Gly Glu Arg Cys Gly Ala Ser Ser
            2690                2695                2700

Phe Thr Cys Ser Asn Gly Arg Cys Ile Ser Glu Glu Trp Lys Cys Asp
2705                2710                2715                2720

Asn Asp Asn Asp Cys Gly Asp Gly Ser Asp Glu Met Glu Ser Val Cys
            2725                2730                2735

Ala Leu His Thr Cys Ser Pro Thr Ala Phe Thr Cys Ala Asn Gly Arg
            2740                2745                2750

Cys Val Gln Tyr Ser Tyr Arg Cys Asp Tyr Tyr Asn Asp Cys Gly Asp
            2755                2760                2765

Gly Ser Asp Glu Ala Gly Cys Leu Phe Arg Asp Cys Asn Ala Thr Thr
            2770                2775                2780

Glu Phe Met Cys Asn Asn Arg Arg Cys Ile Pro Arg Glu Phe Ile Cys
2785                2790                2795                2800

Asn Gly Val Asp Asn Cys His Asp Asn Asn Thr Ser Asp Glu Lys Asn
            2805                2810                2815

Cys Pro Asp Arg Thr Cys Gln Ser Gly Tyr Thr Lys Cys His Asn Ser
            2820                2825                2830

Asn Ile Cys Ile Pro Arg Val Tyr Leu Cys Asp Gly Asp Asn Asp Cys
            2835                2840                2845

Gly Asp Asn Ser Asp Glu Asn Pro Thr Tyr Cys Thr Thr His Thr Cys
```

```
                    2850            2855            2860
Ser Ser Ser Glu Phe Gln Cys Ala Ser Gly Arg Cys Ile Pro Gln His
2865            2870            2875            2880

Trp Tyr Cys Asp Gln Glu Thr Asp Cys Phe Asp Ala Ser Asp Glu Pro
            2885            2890            2895

Ala Ser Cys Gly His Ser Glu Arg Thr Cys Leu Ala Asp Glu Phe Lys
        2900            2905            2910

Cys Asp Gly Gly Arg Cys Ile Pro Ser Glu Trp Ile Cys Asp Gly Asp
        2915            2920            2925

Asn Asp Cys Gly Asp Met Ser Asp Glu Asp Lys Arg His Gln Cys Gln
        2930            2935            2940

Asn Gln Asn Cys Ser Asp Ser Glu Phe Leu Cys Val Asn Asp Arg Pro
2945            2950            2955            2960

Pro Asp Arg Arg Cys Ile Pro Gln Ser Trp Val Cys Asp Gly Asp Val
            2965            2970            2975

Asp Cys Thr Asp Gly Tyr Asp Glu Asn Gln Asn Cys Thr Arg Arg Thr
            2980            2985            2990

Cys Ser Glu Asn Glu Phe Thr Cys Gly Tyr Gly Leu Cys Ile Pro Lys
        2995            3000            3005

Ile Phe Arg Cys Asp Arg His Asn Asp Cys Gly Asp Tyr Ser Asp Glu
        3010            3015            3020

Arg Gly Cys Leu Tyr Gln Thr Cys Gln Gln Asn Gln Phe Thr Cys Gln
3025            3030            3035            3040

Asn Gly Arg Cys Ile Ser Lys Thr Phe Val Cys Asp Glu Asp Asn Asp
            3045            3050            3055

Cys Gly Asp Gly Ser Asp Glu Leu Met His Leu Cys His Thr Pro Glu
            3060            3065            3070

Pro Thr Cys Pro Pro His Glu Phe Lys Cys Asp Asn Gly Arg Cys Ile
        3075            3080            3085

Glu Met Met Lys Leu Cys Asn His Leu Asp Asp Cys Leu Asp Asn Ser
        3090            3095            3100

Asp Glu Lys Gly Cys Gly Ile Asn Glu Cys His Asp Pro Ser Ile Ser
3105            3110            3115            3120

Gly Cys Asp His Asn Cys Thr Asp Thr Leu Thr Ser Phe Tyr Cys Ser
            3125            3130            3135

Cys Arg Pro Gly Tyr Lys Leu Met Ser Asp Lys Arg Thr Cys Val Asp
            3140            3145            3150

Ile Asp Glu Cys Thr Glu Met Pro Phe Val Cys Ser Gln Lys Cys Glu
        3155            3160            3165

Asn Val Ile Gly Ser Tyr Ile Cys Lys Cys Ala Pro Gly Tyr Leu Arg
        3170            3175            3180

Glu Pro Asp Gly Lys Thr Cys Arg Gln Asn Ser Asn Ile Glu Pro Tyr
3185            3190            3195            3200

Leu Ile Phe Ser Asn Arg Tyr Tyr Leu Arg Asn Leu Thr Ile Asp Gly
            3205            3210            3215

Tyr Phe Tyr Ser Leu Ile Leu Glu Gly Leu Asp Asn Val Val Ala Leu
            3220            3225            3230

Asp Phe Asp Arg Val Glu Lys Arg Leu Tyr Trp Ile Asp Thr Gln Arg
        3235            3240            3245

Gln Val Ile Glu Arg Met Phe Leu Asn Lys Thr Asn Lys Glu Thr Ile
        3250            3255            3260

Ile Asn His Arg Leu Pro Ala Ala Glu Ser Leu Ala Val Asp Trp Val
3265            3270            3275            3280
```

-continued

```
Ser Arg Lys Leu Tyr Trp Leu Asp Ala Arg Leu Asp Gly Leu Phe Val
            3285                3290                3295

Ser Asp Leu Asn Gly Gly His Arg Arg Met Leu Ala Gln His Cys Val
            3300                3305                3310

Asp Ala Asn Asn Thr Phe Cys Phe Asp Asn Pro Arg Gly Leu Ala Leu
            3315                3320                3325

His Pro Gln Tyr Gly Tyr Leu Tyr Trp Ala Asp Trp Gly His Arg Ala
            3330                3335                3340

Tyr Ile Gly Arg Val Gly Met Asp Gly Thr Asn Lys Ser Val Ile Ile
3345                3350                3355                3360

Ser Thr Lys Leu Glu Trp Pro Asn Gly Ile Thr Ile Asp Tyr Thr Asn
            3365                3370                3375

Asp Leu Leu Tyr Trp Ala Asp Ala His Leu Gly Tyr Ile Glu Tyr Ser
            3380                3385                3390

Asp Leu Glu Gly His His Arg His Thr Val Tyr Asp Gly Ala Leu Pro
            3395                3400                3405

His Pro Phe Ala Ile Thr Ile Phe Glu Asp Thr Ile Tyr Trp Thr Asp
            3410                3415                3420

Trp Asn Thr Arg Thr Val Glu Lys Gly Asn Lys Tyr Asp Gly Ser Asn
3425                3430                3435                3440

Arg Gln Thr Leu Val Asn Thr Thr His Arg Pro Phe Asp Ile His Val
            3445                3450                3455

Tyr His Pro Tyr Arg Gln Pro Ile Val Ser Asn Pro Cys Gly Thr Asn
            3460                3465                3470

Asn Gly Gly Cys Ser His Leu Cys Leu Ile Lys Pro Gly Gly Lys Gly
            3475                3480                3485

Phe Thr Cys Glu Cys Pro Asp Asp Phe Arg Thr Leu Gln Leu Ser Gly
            3490                3495                3500

Ser Thr Tyr Cys Met Pro Met Cys Ser Ser Thr Gln Phe Leu Cys Ala
3505                3510                3515                3520

Asn Asn Glu Lys Cys Ile Pro Ile Trp Trp Lys Cys Asp Gly Gln Lys
            3525                3530                3535

Asp Cys Ser Asp Gly Ser Asp Glu Leu Ala Leu Cys Pro Gln Arg Phe
            3540                3545                3550

Cys Arg Leu Gly Gln Phe Gln Cys Ser Asp Gly Asn Cys Thr Ser Pro
            3555                3560                3565

Gln Thr Leu Cys Asn Ala His Gln Asn Cys Pro Asp Gly Ser Asp Glu
            3570                3575                3580

Asp Arg Leu Leu Cys Glu Asn His His Cys Asp Ser Asn Glu Trp Gln
3585                3590                3595                3600

Cys Ala Asn Lys Arg Cys Ile Pro Glu Ser Trp Gln Cys Asp Thr Phe
            3605                3610                3615

Asn Asp Cys Glu Asp Asn Ser Asp Glu Asp Ser Ser His Cys Ala Ser
            3620                3625                3630

Arg Thr Cys Arg Pro Gly Gln Phe Arg Cys Ala Asn Gly Arg Cys Ile
            3635                3640                3645

Pro Gln Ala Trp Lys Cys Asp Val Asp Asn Asp Cys Gly Asp His Ser
            3650                3655                3660

Asp Glu Pro Ile Glu Glu Cys Met Ser Ser Ala His Leu Cys Asp Asn
3665                3670                3675                3680

Phe Thr Glu Phe Ser Cys Lys Thr Asn Tyr Arg Cys Ile Pro Lys Trp
            3685                3690                3695
```

-continued

```
Ala Val Cys Asn Gly Val Asp Asp Cys Arg Asp Asn Ser Asp Glu Gln
            3700                3705                3710

Gly Cys Glu Glu Arg Thr Cys His Pro Val Gly Asp Phe Arg Cys Lys
        3715                3720                3725

Asn His His Cys Ile Pro Leu Arg Trp Gln Cys Asp Gly Gln Asn Asp
    3730                3735                3740

Cys Gly Asp Asn Ser Asp Glu Glu Asn Cys Ala Pro Arg Glu Cys Thr
3745                3750                3755                3760

Glu Ser Glu Phe Arg Cys Val Asn Gln Gln Cys Ile Pro Ser Arg Trp
            3765                3770                3775

Ile Cys Asp His Tyr Asn Asp Cys Gly Asp Asn Ser Asp Glu Arg Asp
        3780                3785                3790

Cys Glu Met Arg Thr Cys His Pro Glu Tyr Phe Gln Cys Thr Ser Gly
    3795                3800                3805

His Cys Val His Ser Glu Leu Lys Cys Asp Gly Ser Ala Asp Cys Leu
    3810                3815                3820

Asp Ala Ser Asp Glu Ala Asp Cys Pro Thr Arg Phe Pro Asp Gly Ala
3825                3830                3835                3840

Tyr Cys Gln Ala Thr Met Phe Glu Cys Lys Asn His Val Cys Ile Pro
            3845                3850                3855

Pro Tyr Trp Lys Cys Asp Gly Asp Asp Asp Cys Gly Asp Gly Ser Asp
        3860                3865                3870

Glu Glu Leu His Leu Cys Leu Asp Val Pro Cys Asn Ser Pro Asn Arg
    3875                3880                3885

Phe Arg Cys Asp Asn Asn Arg Cys Ile Tyr Ser His Glu Val Cys Asn
    3890                3895                3900

Gly Val Asp Asp Cys Gly Asp Gly Thr Asp Glu Thr Glu His Cys
3905                3910                3915                3920

Arg Lys Pro Thr Pro Lys Pro Cys Thr Glu Tyr Glu Tyr Lys Cys Gly
            3925                3930                3935

Asn Gly His Cys Ile Pro His Asp Asn Val Cys Asp Asp Ala Asp Asp
        3940                3945                3950

Cys Gly Asp Trp Ser Asp Glu Leu Gly Cys Asn Lys Gly Lys Glu Arg
    3955                3960                3965

Thr Cys Ala Glu Asn Ile Cys Glu Gln Asn Cys Thr Gln Leu Asn Glu
    3970                3975                3980

Gly Gly Phe Ile Cys Ser Cys Thr Ala Gly Phe Glu Thr Asn Val Phe
3985                3990                3995                4000

Asp Arg Thr Ser Cys Leu Asp Ile Asn Glu Cys Glu Gln Phe Gly Thr
            4005                4010                4015

Cys Pro Gln His Cys Arg Asn Thr Lys Gly Ser Tyr Glu Cys Val Cys
        4020                4025                4030

Ala Asp Gly Phe Thr Ser Met Ser Asp Arg Pro Gly Lys Arg Cys Ala
    4035                4040                4045

Ala Glu Gly Ser Ser Pro Leu Leu Leu Leu Pro Asp Asn Val Arg Ile
    4050                4055                4060

Arg Lys Tyr Asn Leu Ser Ser Glu Arg Phe Ser Glu Tyr Leu Gln Asp
4065                4070                4075                4080

Glu Glu Tyr Ile Gln Ala Val Asp Tyr Asp Trp Asp Pro Lys Asp Ile
            4085                4090                4095

Gly Leu Ser Val Val Tyr Tyr Thr Val Arg Gly Glu Gly Ser Arg Phe
        4100                4105                4110

Gly Ala Ile Lys Arg Ala Tyr Ile Pro Asn Phe Glu Ser Gly Arg Asn
```

-continued

```
            4115               4120                4125

Asn Leu Val Gln Glu Val Asp Leu Lys Leu Lys Tyr Val Met Gln Pro
            4130               4135                4140

Asp Gly Ile Ala Val Asp Trp Val Gly Arg His Ile Tyr Trp Ser Asp
4145                4150                4155                4160

Val Lys Asn Lys Arg Ile Glu Val Ala Lys Leu Asp Gly Arg Tyr Arg
            4165                4170                4175

Lys Trp Leu Ile Ser Thr Asp Leu Asp Gln Pro Ala Ile Ala Val
            4180                4185                4190

Asn Pro Lys Leu Gly Leu Met Phe Trp Thr Asp Trp Gly Lys Glu Pro
            4195                4200                4205

Lys Ile Glu Ser Ala Trp Met Asn Gly Glu Asp Arg Asn Ile Leu Val
            4210                4215                4220

Phe Glu Asp Leu Gly Trp Pro Thr Gly Leu Ser Ile Asp Tyr Leu Asn
4225                4230                4235                4240

Asn Asp Arg Ile Tyr Trp Ser Asp Phe Lys Glu Asp Val Ile Glu Thr
            4245                4250                4255

Ile Lys Tyr Asp Gly Thr Asp Arg Arg Val Ile Ala Lys Glu Ala Met
            4260                4265                4270

Asn Pro Tyr Ser Leu Asp Ile Phe Glu Asp Gln Leu Tyr Trp Ile Ser
            4275                4280                4285

Lys Glu Lys Gly Glu Val Trp Lys Gln Asn Lys Phe Gly Gln Gly Lys
            4290                4295                4300

Lys Glu Lys Thr Leu Val Val Asn Pro Trp Leu Thr Gln Val Arg Ile
4305                4310                4315                4320

Phe His Gln Leu Arg Tyr Asn Lys Ser Val Pro Asn Leu Cys Lys Gln
            4325                4330                4335

Ile Cys Ser His Leu Cys Leu Leu Arg Pro Gly Gly Tyr Ser Cys Ala
            4340                4345                4350

Cys Pro Gln Gly Ser Ser Phe Ile Glu Gly Ser Thr Thr Glu Cys Asp
            4355                4360                4365

Ala Ala Ile Glu Leu Pro Ile Asn Leu Pro Pro Pro Cys Arg Cys Met
            4370                4375                4380

His Gly Gly Asn Cys Tyr Phe Asp Glu Thr Asp Leu Pro Lys Cys Lys
4385                4390                4395                4400

Cys Pro Ser Gly Tyr Thr Gly Lys Tyr Cys Glu Met Ala Phe Ser Lys
            4405                4410                4415

Gly Ile Ser Pro Gly Thr Thr Ala Val Ala Val Leu Leu Thr Ile Leu
            4420                4425                4430

Leu Ile Val Val Ile Gly Ala Leu Ala Ile Ala Gly Phe Phe His Tyr
            4435                4440                4445

Arg Arg Thr Gly Ser Leu Leu Pro Ala Leu Pro Lys Leu Pro Ser Leu
            4450                4455                4460

Ser Ser Leu Val Lys Pro Ser Glu Asn Gly Asn Gly Val Thr Phe Arg
4465                4470                4475                4480

Ser Gly Ala Asp Leu Asn Met Asp Ile Gly Val Ser Gly Phe Gly Pro
            4485                4490                4495

Glu Thr Ala Ile Asp Arg Ser Met Ala Met Ser Glu Asp Phe Val Met
            4500                4505                4510

Glu Met Gly Lys Gln Pro Ile Ile Phe Glu Asn Pro Met Tyr Ser Ala
            4515                4520                4525

Arg Asp Ser Ala Val Lys Val Val Gln Pro Ile Gln Val Thr Val Ser
            4530                4535                4540
```

```
Glu Asn Val Asp Asn Lys Asn Tyr Gly Ser Pro Ile Asn Pro Ser Glu
4545                4550                4555                4560

Ile Val Pro Glu Thr Asn Pro Thr Ser Pro Ala Ala Asp Gly Thr Gln
                4565                4570                4575

Val Thr Lys Trp Asn Leu Phe Lys Arg Lys Ser Lys Gln Thr Thr Asn
            4580                4585            4590

Phe Glu Asn Pro Ile Tyr Ala Gln Met Glu Asn Glu Gln Lys Glu Ser
        4595                4600            4605

Val Ala Ala Thr Pro Pro Ser Pro Ser Leu Pro Ala Lys Pro Lys
        4610            4615            4620

Pro Pro Ser Arg Arg Asp Pro Thr Pro Thr Tyr Ser Ala Thr Glu Asp
4625            4630            4635                4640

Thr Phe Lys Asp Thr Ala Asn Leu Val Lys Glu Asp Ser Glu Val
                4645            4650                4655
```

METHOD FOR ESTIMATING GFR (GLOMERULAR FILTRATION RATE) FROM MEASURED VALUE OF MEGALIN IN URINE

CROSS-REFERENCE TO RELATED APPLICATIONS

This application is a National Stage application of PCT/JP2014/053871, filed Feb. 19, 2014, which claims priority from Japanese application JP 2013-030206, filed Feb. 19, 2013.

The instant application contains a Sequence Listing which has been submitted in ASCII format via EFS-WEB and is hereby incorporated by reference in its entirety. Said ASCII copy, created on Aug. 17, 2015, is named sequence.txt and is 56 KB.

TECHNICAL FIELD

The present invention relates to a method for estimating a glomerular filtration rate (GFR) from a measured value of megalin in urine.

BACKGROUND ART

The number of end-stage kidney disease (ESKD) patients in need of dialysis or transplantation has been increasing all over the world. During the 10 years from 1990 to 2000, the number of ESKD patients increased from 430,000 to 1,065,000. In 2008, the number reached at least about 1,650,000. In 2011, the number of patients receiving maintenance dialysis reached approximately 300,000 in Japan. This means that the number of patients per million people is 2,126, which is the second-highest such figure in the world. Chronic kidney diseases (CKDs) are preliminary forms of ESKDs that have been increasing all over the world. The number of CKD patients in the U.S. in 2000 was estimated to account for 13.07% (25,610,000 individuals) of the adult population. The number of CKD patients in Japan in 2005 accounted for 12.9% (13,300,000 individuals) of the adult population. The number of CKD patients and patients with preliminary forms of CKDs is said to have reached as high as 20,000,000. In addition, CKDs are risk factors for cardiovascular diseases (CVDs). In Western countries, the number of CKD patients who die due to CVDs is greater than the number of CKD patients who start dialysis. Also in Japan, CKDs are risk factors for CVDs. Meanwhile, if each CKD patient could receive adequate treatment in accordance with his/her own disease state, it would be possible to significantly reduce the number of patients who start dialysis or die due to heart diseases. For such purpose, adequate evaluation methods are necessary. In the existing test methods, the glomerular filtration rate (GFR) can be used for accurate renal function assessment. The term "glomerular filtration rate" refers to the volume of serum filtered through all glomeruli of the kidneys per unit of time. A decline in the renal function due to renal failure or the like is associated with a decline in the filtration capacity of glomeruli. Therefore, the degree of deterioration of the renal function can be confirmed by determining GFR. In order to accurately determine GFR, inulin clearance measurement with the use of inulin is recommended. However, since inulin clearance measurement is complex, creatinine clearance based on the creatinine level and estimated glomerular filtration rate (eGFR) are used in clinical practice. In order to obtain the creatinine clearance or eGFR, it is necessary to obtain the serum creatinine level. Serum creatinine testing is invasive and thus imposes a significant burden on patients. That is, if GFR could be estimated in a non-invasive manner, it would be beneficial to patients.

Megalin in urine is a substance observed in association with renal diseases. Convenient renal disorder tests involving measurement of urinary megalin have been disclosed (Patent Documents 1 and 2).

Megalin also known as Glycoprotein 330 (gp330) or Low Density Lipoprotein (LDL)-receptor relate protein 2 (LRP2) is a glycoprotein having a molecular weight of about 600 kDa, which is expressed in renal proximal tubular epithelial cells (Non-patent Documents 1 and 2).

As a result of cell culture experiments using renal proximal tubular epithelial cells, the presence of two types of megalin, membrane-bound full length megalin and soluble-form megalin (fragment containing the extracellular domain) lacking the intracellular domain, is known (Non-patent Document 3). A method for measuring urinary full-length human megalin, the extracellular domain thereof, and the intracellular domain thereof has also been reported (Patent Document 3).

PRIOR ART DOCUMENTS

Patent Documents

Patent Document 1: WO2002/037099
Patent Document 2: WO2010/126055
Patent Document 3: WO2010/126043

Non-Patent Documents

Non-Patent Document 1: Christensen E. I., Willnow T. E. (1999), J. Am. Soc. Nephrol. 10, 2224-2236
Non-Patent Document 2: Zheng G, McCluskey R. T. et al. (1994), J. Histochem. Cytochem. 42, 531-542
Non-Patent Document 3: Flavia F. J., Julie R. I. et al. (1998), Kidney. International. 53, 358-366

SUMMARY OF THE INVENTION

Problem to be Solved by the Invention

The object of the present invention is to provide a method for estimating GFR without the use of creatinine serum.

Means for Solving the Problem

As a result of intensive studies to achieve the above object, the present inventors found that there is a high correlation between the urinary megalin excretion rate and the estimated glomerular filtration rate (eGFR) in renal disease patients, and the glomerular filtration rate (GFR) can be estimated with high accuracy in a non-invasive manner by measuring the urinary megalin level. This has led to the completion of the present invention.

Specifically, the present invention is as follows.

[1] A method for estimating a glomerular filtration rate from a measured value of megalin in urine.

[2] The method for estimating a glomerular filtration rate according to [1], wherein the measured value of megalin in urine is associated with the glomerular filtration rate for estimation of the glomerular filtration rate from the measured value of megalin in urine based on the association.

[3] The method for estimating a glomerular filtration rate according to [1] or [2], wherein the measured value of megalin in urine is associated with the glomerular filtration rate by regression analysis.

[4] The method for estimating a glomerular filtration rate according to any one of [1] to [3], wherein the measured value of megalin in urine is a urinary megalin excretion rate corrected with a urinary creatinine concentration.

[5] The method for estimating a glomerular filtration rate according to any one of [1] to [4], wherein the glomerular filtration rate is obtained based on inulin clearance.

[6] The method for estimating a glomerular filtration rate according to any one of [1] to [4], wherein the glomerular filtration rate is obtained based on creatinine clearance.

[7] The method for estimating a glomerular filtration rate according to any one of [1] to [4], wherein the glomerular filtration rate is obtained from an estimated glomerular filtration rate.

[8] The method for estimating a glomerular filtration rate according to any one of [1] to [7], wherein megalin in urine is an extracellular domain fragment of urinary megalin.

This description includes all or part of the contents as disclosed in the description and/or drawings of Japanese Patent Application No. 2013-030206, which is a priority document of the present application.

Advantageous Effects of Invention

According to the method for estimating the glomerular filtration rate (GFR) based on the measured value of megalin in urine of the present invention, GFR, which in the past has been measured by invasive tests or obtained as eGFR, can be estimated in a non-invasive manner.

DESCRIPTION OF EMBODIMENTS

Figure 1:
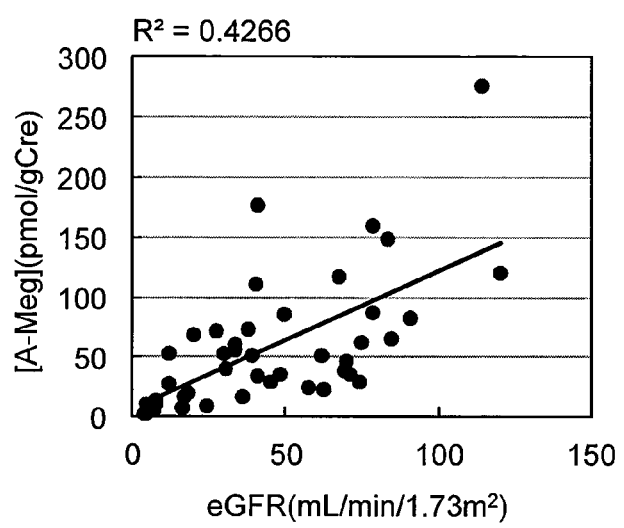
FIG. 1 shows the relationship between the urinary megalin excretion rate and eGFR in renal disease patients (Example 2 and the Comparative Example).

According to the method of the present invention, the glomerular filtration rate (GFR) is estimated from the measured value of megalin in urine of a subject with high accuracy.

Full-length human megalin comprises an amino acid sequence of amino acids 26 to 4655 of the amino acid sequence as shown in SEQ ID NO: 2. SEQ ID NO: 1 shows the nucleotide sequence of human megalin. The sequence of amino acids 1 to 25 of the amino acid sequence as shown in SEQ ID NO: 2 is a signal peptide sequence. The amino acid sequence of human megalin is disclosed under Accession No: NP_004516 (RefSeq protein ID: 126012573) in the National Center for Biotechnology Information (NCBI). Human megalin is a single-pass transmembrane glycoprotein composed of the following three domains: an extracellular domain; a transmembrane domain; and an intracellular domain. A domain consisting of amino acids 26 to 4424 of the amino acid sequence as shown in SEQ ID NO: 2 is referred to as a human megalin extracellular domain. In addition, a domain consisting of amino acids 4447 to 4655 of the amino acid sequence as shown in SEQ ID NO: 2 is referred to as a human megalin intracellular domain. Similarly, a domain consisting of amino acids 4425 to 4446 of the amino acid sequence as shown in SEQ ID NO: 2 is referred to as a human megalin transmembrane domain. The term "human megalin extracellular domain fragment" refers to a fragment comprising the whole or part of an extracellular domain, which is the whole or part of a domain consisting of amino acids 26 to 4424 of the amino acid sequence as shown in SEQ ID NO: 2, and lacks an intracellular domain. An example of a human megalin extracellular domain fragment lacking an intracellular domain is a fragment consisting of an amino acid sequence of amino acids 26 to 4361 of the amino acid sequence as shown in SEQ ID NO: 2. Such fragment is a remnant extracellular domain fragment generated during a process of preparation of a primary cleavage product consisting of amino acids 4362 to 4655 of the amino acid sequence as shown in SEQ ID NO: 2. A further example of a human megalin extracellular domain fragment lacking an intracellular domain is a fragment consisting of an amino acid sequence of amino acids 4362 to 4437 of the amino acid sequence as shown in SEQ ID NO: 2. Such fragment is a remnant extracellular domain fragment generated during a process of preparation of a secondary cleavage product consisting of amino acids 4438 to 4655 of the amino acid sequence as shown in SEQ ID NO: 2.

In the present invention, the measurement of megalin excreted in the urine is performed. Megalin subjected to measurement may be full-length megalin, the extracellular domain thereof, or the intracellular domain thereof, and it is preferably the extracellular domain. Urine specified herein as a specimen can be obtained from any subject. Any method for collecting urine may be employed herein. Morning urine or spot urine is preferably used. In addition, the amount of urine required for the method of the present invention ranges from about 10 μL to 200 μL. The test method of the present invention may be performed together with other general urine tests.

Urine used as a specimen can be processed by adding a treatment liquid to collected urine, followed by mixing. The treatment liquid may be any liquid as long as it allows adjustment of urine pH, masking of urine sediment, and/or solubilization of megalin. However, a preferable example is a solution obtained by adding a chelating agent, a surfactant, and the like to a buffer solution. A buffer solution or a chelating agent may be any known product while a surfactant to be used is preferably a non-ionic surfactant. An example of a treatment liquid is a solution containing 2M Tris-HCl (pH 8.0), 0.2M EDTA, and 10% (vol./vol.) Triton X-100. A urine sample solution can be obtained by adding 10 μl of such treatment liquid to 90 μL of a urine specimen, followed by mixing.

Various methods can be used for detecting megalin from a urine sample solution. An example of a method for detecting megalin is an immunological technique. An immunological technique can be performed by immunostaining methods (including a fluorescent antibody technique, an enzyme antibody method, a heavy metal-labeled antibody method, and a radioisotope-labeled antibody method), methods using a combination of separation by electrophoresis and detection using fluorescence, enzyme, and radioisotope etc., (including Western blot method and fluorescence two-dimensional electrophoresis), an enzyme-linked immunosorbent assay (ELISA) method, a dot blotting method, a latex agglutination method (LA: Latex Agglutination-Turbidimetric Immunoassay), immunochromatography method, or the like. Preferably, ELISA methods or LA methods are employed. Among ELISA methods, a sandwich method is preferably employed from a quantitative viewpoint. In the case of a sandwich method, a urine sample solution is added to a microtiter plate to which an anti-megalin antibody has been immobilized for antigen-antibody reaction to take place, an enzyme-labeled anti-megalin antibody is further added for an antigen-antibody reaction to take place, washing is performed, the resultant is reacted with an enzyme substrate for color development, absorbance is measured, and thus urinary megalin is detected and the concentration of urinary megalin can be calculated from the measured value. Moreover, an antigen-antibody reaction is performed using a fluorescence-labeled anti-megalin antibody, and then fluorescence can be measured.

An anti-megalin antibody that is used in an immunological technique may be an antibody with which human megalin can be recognized and detected. An anti-megalin antibody that is used in the present invention may be a known antibody or an antibody that could be developed in the future. Examples of an anti-megalin antibody include, but are not particularly limited to: a monoclonal antibody, a polyclonal antibody, a chimeric antibody, a humanized antibody, and fragments thereof with binding activity. In addition, a megalin domain to be recognized is mot limited. Thus, either an antibody that recognizes an extracellular domain or an antibody that recognizes an intracellular domain can be used. These antibodies may be labeled with enzymes or fluorescent dyes. In addition, 2 or more types of anti-megalin antibody may be used. Two (2) or more types of anti-megalin antibody are used for the above sandwich method, and are preferably antibodies that recognize epitopes differing from each other. For example, as an anti-megalin antibody, an antibody against a megalin extracellular domain fragment can be used. Specifically, two or more types of anti-megalin antibodies that recognize different epitopes selected from among epitopes located in a domain (LBD1) consisting of amino acids 26 to 314 in the extracellular domain of the amino acid the amino acid sequence as shown in SEQ ID NO: 2 can be used.

According to the present invention, the urinary megalin level means the measured value of megalin in urine. It may be the urinary megalin concentration or a value obtained by correcting the urinary megalin concentration with the values of urine components that are stably excreted in the urine (urine component values).

A particularly preferable urine component is urinary creatinine. It is preferable to correct the urinary megalin concentration with the urinary creatinine concentration. It is thought that the urinary creatinine concentration is substantially constant for each individual regardless of disease because creatinine production depends on muscle amount. When testing urine components, it is common to use a technique for correcting the amount of a urine component of interest based on the amount per 1 g of creatinine in order to avoid the influence of urine dilution or concentration. This allows comparison of urine components per unit gram of creatinine. The value obtained by correcting the urinary megalin concentration with the urinary creatinine concentration is referred to as the urinary megalin excretion rate (MEG/Cre), and it can be calculated with the following equation.

Urinary megalin excretion rate (pmol/gCre)=100× Urinary megalin concentration (pM)/Urinary creatinine concentration (mg/dL)  <Equation>MEG/Cre:

According to the method of the present invention, the measured value of megalin in urine is associated with the glomerular filtration rate to estimate the glomerular filtration rate based on the measured value of megalin in urine.

In order to accurately determine the glomerular filtration rate (GFR), creatinine clearance can be used, as well as inulin clearance. Further, the estimated glomerular filtration rate (eGFR) can be used as the glomerular filtration rate.

The estimated glomerular filtration rate (eGFR) can be obtained using the following predictive equation disclosed in March 2008 in the "Japanese Equation for Estimating GFR" project launched by the Japanese Society of Nephrology based on the serum creatinine level and age. eGFR (mL/min/1.73 m$^2$)=194×Cr$^{-1.094}$×Age$^{-0.287}$ (where "Cr" means the serum creatinine level and "Age" means the subject's age) (If the subject is a female, the solution is further multiplied by 0.739.)

There is a positive correlation between eGFR obtained as a result of estimation by the above equation and the urinary megalin excretion rate expressed as "pmol/gCre" above. For example, when the urinary megalin excretion rate is 0-100 pmol/gCre and eGFR is 0-150 mL/min/1.73 m$^2$, R$^2$ (where R represents a correlation coefficient) is 0.3 or more and preferably 0.4 or more. As the urinary megalin excretion rate increases, eGFR also increases. The term "eGFR" represents the estimated value of GFR. Since there is a high correlation between the urinary megalin excretion rate and eGFR, it is possible to estimate GFR from the urinary megalin excretion rate with high accuracy. GFR estimated by the method of the present invention is highly likely to approximate actual GFR. In this regard, GFR can be estimated with high probability by the method of the present invention.

It is possible to associate the measured value of megalin in urine with the glomerular filtration rate by, for example, obtaining an equation showing the relationship between the measured value of megalin in urine and eGFR through regression analysis. eGFR can be obtained from the urinary megalin excretion rate based on the obtained regression equation. GFR can be estimated based on eGFR. The present invention also encompasses a method for determining the measured value of megalin in urine and eGFR or GFR for a plurality of subjects and obtaining a regression equation representing the relationship between the measured value of megalin and eGFR or GFR through regression analysis so as to obtain a calculation formula that is used for estimating eGFR or GFR from the measured value of megalin in urine.

The above equation for obtaining eGFR is intended to be used for Japanese people. eGFR, however, can be estimated based on the serum creatinine level and age regardless of race. That is, GFR can be estimated from the urinary megalin excretion rate regardless of race.

It is also possible to associate the measured value of megalin in urine with the glomerular filtration rate determined with the use of inulin clearance or creatinine clearance so as to estimate the glomerular filtration rate from the measured value of megalin in urine based on the obtained association.

A decrease in GFR estimated from the measured value of megalin in urine means a decrease in the renal function. Thus, it is possible to select a therapy and the like for a patient with decreased renal function based on GFR estimated by the method of the present invention.

EXAMPLES

The present invention is described in detail with reference to examples of the present invention. However, the present invention is not limited thereto and various applications of the present invention are feasible within the technical idea of the present invention.

Example 1

Determination of the Urinary Megalin Excretion Rate

The rate of excretion of a fragment (the extracellular domain of megalin) containing human megalin extracellular domain in the urine was determined using a monoclonal antibody (anti-megalin extracellular domain monoclonal antibody) against the human megalin extracellular domain. The anti-megalin extracellular domain monoclonal antibody is a mouse monoclonal antibody that recognizes an epitope that is present in the domain (LBD1) consisting of amino acids 26 and 314 of the amino acid sequence as shown in SEQ ID NO: 2. Determination and evaluation were carried out using an anti-human megalin LBD1 monoclonal antibody A and an anti-human megalin LBD1 monoclonal antibody B recognizing two different epitopes in LBD1. The human megalin extracellular domain-containing fragment in the urine was measured using a microtiter plate onto which an anti-human megalin LBD1 monoclonal antibody A had been immobilized, and an ALP (alkaline phosphatase)-labeled anti-human megalin LBD1 monoclonal antibody B.

First, 90 μL of urine and 10 μL of a solution comprising 2 M Tris-HCl, 0.2 M ethylenediamine-N,N,N',N'-tetraacetic acid (hereafter abbreviated as "EDTA"), 10% (vol./vol.) polyethylene glycol mono-p-isooctylphenyl ether (hereinafter, polyethylene glycol mono-p-isooctylphenyl ether is referred to as Triton X-100) (pH 8.0) were mixed. The mixed solution (100 μL) was added to wells of the microtiter plate onto which an anti-human megalin LBD1 monoclonal antibody A had been immobilized (FluoroNunc (Trademark) Module F16 Black-Maxisorp (Trademark) Surface plate, Nalge Nunc International), and then left to stand at 37° C. for 1 hour. Subsequently, the urine sample solution that had been added to wells was removed by decantation. TBS-T was added at 200 μL/well to the wells of the microtiter plate, and then removed by decantation, followed by washing. The washing step was performed 3 times in total. Subsequently, an ALP-labeled anti-human megalin LBD1 monoclonal antibody B (0.5 ng/mL) solution was added at 100 μL/well. The ALP-labeled anti-human megalin LBD1 monoclonal antibody B was prepared with a diluent for a labeled antibody. The resultant was left to stand at 37° C. for 1 hour, and then the ALP-labeled antibody solution that had been added to wells was removed by decantation. TBS-T was added at 200 μL/well to the wells of the microtiter plate, and then removed by decantation, followed by washing. The washing step was performed 4 times in total. Subsequently, an assay buffer was added at 200 μL/well to the wells of the microtiter plate, and then removed by decantation, followed by washing. The washing step was performed 2 times in total. Next, CDP-Star (registered trademark) Chemiluminescent Substrate for Alkaline Phosphatase Ready-to-Use (0.4 mM) with Emerald-II (trademark) Enhancer (ELISA-Light (trademark) System: Applied Biosystems) was added as a substrate solution for ALP enzymatic reaction to wells at 100 μL/well, and then left to stand at 37° C. for 30 minutes while protecting the solution from light. Immediately after the procedure, the cumulative emission intensity of the wells was measured for 1 second. The measured values were used as indicators for evaluation of the measurement of urinary megalin. Microplate Luminometer Centro LB960 and MicroWin2000 software (Berthold) were used for measuring chemiluminescence intensity. As the reference sample for the calibration curve, native human megalin extracted from the kidney was used. The urinary megalin excretion rate was calculated by the following equation by correcting the urinary megalin concentration with the urinary creatinine concentration.

Urinary megalin excretion rate (pmol/g)=100×Urinary megalin concentration (pM)/Urinary creatinine concentration (mg/dL)   <Equation>MEG/Cre:

Example 2

Relationship Between the Urinary Megalin Excretion Rate and the Estimated Glomerular Filtration Rate (eGFR)

The megalin concentrations in 45 cases of renal disease patients were determined by the method specified in Example 1 to obtain the urinary megalin excretion rates. In addition, eGFR was obtained using the following predictive equation disclosed in March 2008 in the "Japanese Equation for Estimating GFR" project launched by the Japanese Society of Nephrology.

eGFR (mL/min/1.73 m$^2$)=194×Cr$^{-1.094}$×Age$^{-0.287}$ (where "Cr" means the serum creatinine level and "Age" means the subject's age) (If the subject is a female, the solution is further multiplied by 0.739.)

FIG. 1 shows the relationship between the urinary megalin excretion rate and eGFR. FIG. 1 revealed that there is a high correlation between the urinary megalin excretion rate and eGFR ($R^2$=0.4266). That is, eGFR can be estimated from the measured value of megalin in urine.

Comparative Example

Relationship Between Other Renal Disease Markers and eGFR

The urinary megalin excretion rates in 45 cases of renal disease patients were determined by the method specified in Example 1. In addition, eGFR was obtained using the predictive equation disclosed in March 2008 in the "Japanese Equation for Estimating GFR" project launched by the Japanese Society of Nephrology.

Further, measurement was performed for al-microglobulin (AMG), β2-microglobulin (BMG), and N-acetyl-β-D-glucosaminidase (NAG), which are proximal tubular defect markers, as well as urinary megalin. Since these AMG, BMG, and NAG are urine markers, they are corrected with the urinary creatinine level. Measurement of AMG, BMG, and NAG was performed using commercially available kits.

Figure 2:
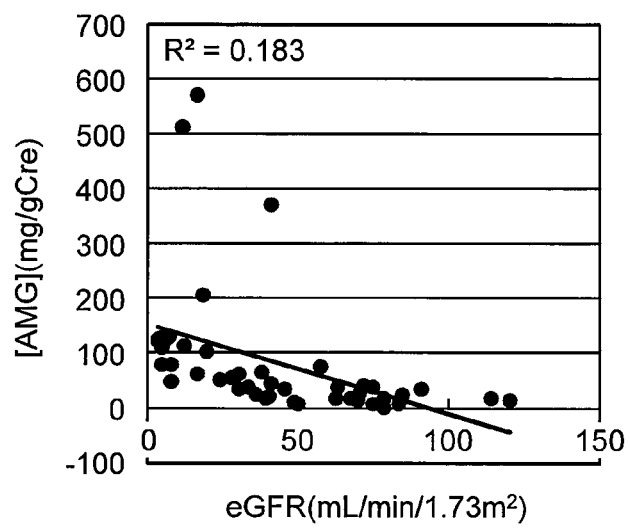
FIG. 2 shows the relationship between α1-microglobulin and eGFR in renal disease patients (the Comparative Example).
Figure 3:
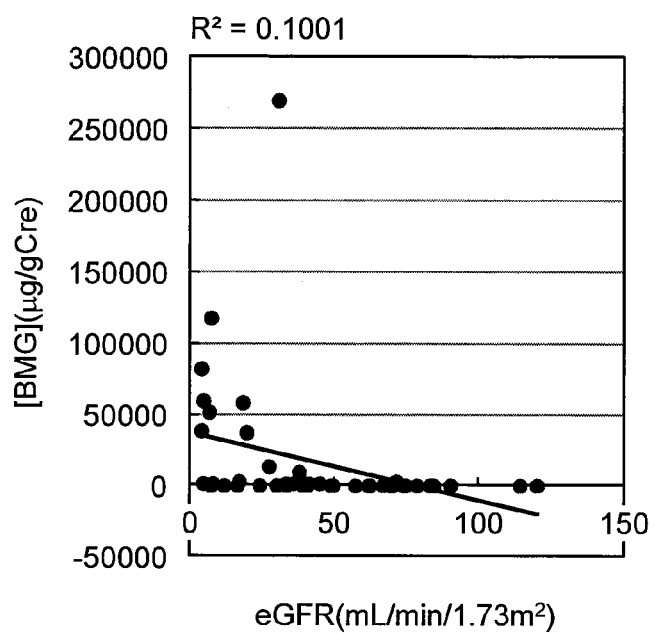
FIG. 3 shows the relationship between β2-microglobulin and eGFR in renal disease patients (the Comparative Example).
Figure 4:
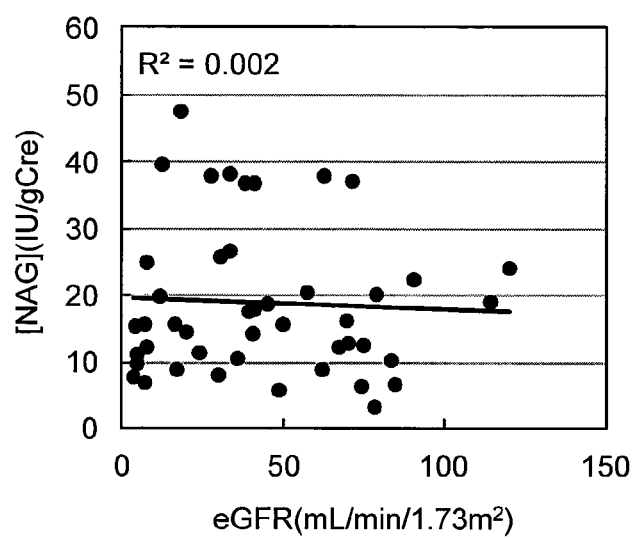
FIG. 4 shows the relationship between N-acetyl-β-D-glucosaminidase and eGFR in renal disease patients (the Comparative Example).

FIGS. 2, 3, and 4 show the relationships between eGFR and AMG, eGFR and BMG, and eGFR and NAG, respectively.

The results of Example 2 and the Comparative Example revealed that the highest correlation was observed between eGFR and urinary megalin from among four different urine markers, including urinary megalin. That is, although urinary megalin is a proximal tubular defect marker, it is a marker capable of estimating eGFR with high accuracy.

INDUSTRIAL APPLICABILITY

As explained above, with the use of the present invention, it is possible to estimate GFR with high accuracy by measuring megalin in urine. In addition, since urine is used as a sample in the test method of the present invention, the test can be performed in a non-invasive manner, unlike testing with the conventional methods. This allows reduction of the physical burdens imposed on patients, which is advantageous.

All publications, patents, and patent applications cited herein are incorporated herein by reference in their entirety.

The invention claimed is:

1. A method for estimating a glomerular filtration rate, which comprises associating the measured value of megalin in urine with the glomerular filtration rate by regression analysis and estimating the glomerular filtration rate from the measured value of megalin in urine based on the association between the measured value of megalin in urine and the glomerular filtration rate, wherein megalin in urine is an extracellular domain fragment of urinary megalin, and there is a positive correlation between the glomerular filtration rate and the measured value of megalin.

2. The method for estimating a glomerular filtration rate according to claim 1, wherein the measured value of megalin in urine is a urinary megalin excretion rate corrected with a urinary creatinine concentration.

3. The method for estimating a glomerular filtration rate according to claim 1, wherein the glomerular filtration rate is obtained based on inulin clearance.

4. The method for estimating a glomerular filtration rate according to claim 1, wherein the glomerular filtration rate is obtained based on creatinine clearance.

5. The method for estimating a glomerular filtration rate according to claim 1, wherein the glomerular filtration rate is obtained from an estimated glomerular filtration rate.

* * * * *